United States Patent
Kawabe

[11] Patent Number: 6,080,897
[45] Date of Patent: Jun. 27, 2000

[54] METHOD FOR PRODUCING MONOETHYLENE GLYCOL

[75] Inventor: Kazuki Kawabe, Mie, Japan

[73] Assignee: Mitsubishi Chemical Corporation, Tokyo, Japan

[21] Appl. No.: 09/271,435

[22] Filed: Mar. 18, 1999

[30] Foreign Application Priority Data

Mar. 19, 1998 [JP] Japan ................... 10-069985
Jan. 26, 1999 [JP] Japan ................... 11-016728

[51] Int. Cl.$^7$ .................................................. C07C 27/00
[52] U.S. Cl. ............................................ 568/858; 549/230
[58] Field of Search ............................. 568/858; 549/230

[56] References Cited

U.S. PATENT DOCUMENTS

| | | | |
|---|---|---|---|
| 3,922,314 | 11/1975 | Cocuzza | 568/858 |
| 4,160,116 | 7/1979 | Mieno | 568/858 |
| 4,283,580 | 8/1981 | Odanaka | 568/858 |
| 4,314,945 | 2/1982 | McMullen | 568/858 |
| 4,400,559 | 8/1983 | Bhise | 568/858 |
| 4,556,748 | 12/1985 | Tsang | 568/858 |
| 4,599,467 | 7/1986 | Kersten | 568/858 |
| 5,508,442 | 4/1996 | Wagner | 568/858 |
| 5,763,691 | 6/1998 | Kawabe | 568/858 |

*Primary Examiner*—Michael L. Shippen
*Attorney, Agent, or Firm*—Oblon, Spivak, McClelland, Maier & Neustadt, P.C.

[57] ABSTRACT

Disclosed is a method for producing monoethylene glycol, which is a method for producing ethylene glycol that comprises a carbonation step in which ethylene oxide is allowed to react with carbon dioxide in the presence of a carbonation catalyst thereby effecting formation of a reaction solution containing ethylene carbonate, a hydrolysis step in which the reaction solution is converted into an ethylene glycol aqueous solution by hydrolyzing ethylene carbonate in the reaction solution and a distillation step in which purified ethylene glycol and a catalyst solution containing the carbonation catalyst are obtained from the ethylene glycol aqueous solution by distillation, wherein the improvement resides in that the reaction is carried out in the presence of a carbonation catalyst using a bubble column reactor by supplying ethylene oxide, carbon dioxide and water into the reactor.

10 Claims, 2 Drawing Sheets

METHOD FOR PRODUCING MONOETHYLENE GLYCOL

BACKGROUND OF THE INVENTION

This invention relates to a method for the production of monoethylene glycol. More particularly, it relates to the improvement of a method in which monoethylene glycol is selectively produced from ethylene oxide via ethylene carbonate.

Monoethylene glycol is broadly used in polyester, polyurethane, non-freezing solution, cellophane, unsaturated polyester and the like.

Production of monoethylene glycol from ethylene oxide is generally carried out by hydrating to ethylene oxide in the absence of catalyst. The thus obtained hydration product is concentrated and then completely dehydrated by rectification while separating byproducts to obtain high purity monoethylene glycol.

In the hydration process of ethylene oxide, successive reaction of unreacted ethylene oxide with formed monoethylene glycol occurs and, as the result, diethylene glycol, triethylene glycol and more higher polyglycols are formed as by-products in addition to monoethylene glycol. In order to obtain monoethylene glycol most in demand with a high yield, it is necessary to supply large excess of water to reduce the successive reaction, generally from 10 to 25 moles of water based on 1 mole of ethylene oxide.

However, the addition of excess water for the purpose of improving the yield causes dilution of product in the formed solution, so that a large quantity of energy is required for removing the excess water in the distillation step.

In addition, the yield of monoethylene glycol obtained in this manner is merely around 90% which is not satisfactory.

In order to avoid such problems, a method has been proposed (JP-A-54-98765 (U.S. Pat. No. 4,314,945); the term "JP-A" as used herein means an "unexamined published Japanese patent application") in which monoethylene glycol is selectively obtained by producing ethylene carbonate from ethylene oxide and carbon dioxide (JP-A-57-31682) and then hydrolyzing ethylene carbonate (JP-A-55-154928 (U.S. Pat. No. 4,283,580)).

An advantage of this method is that the side reaction which generates diethylene glycol from monoethylene glycol and ethylene oxide does not occur and monoethylene glycol therefore is obtained with a markedly high yield, because the reaction for the formation of monoethylene glycol is carried out after ethylene oxide is once converted completely into ethylene carbonate.

However, the reaction for the production of ethylene carbonate from ethylene oxide is slow and requires isolation of ethylene oxide prior to the reaction.

As reactors for use in the production of the intermediate product ethylene carbonate, serial arrangement of a plurality of tube type reactors and condensers (Springmann, *Fette Seifen Anstrichmittel*, 73, 394–399 (1971)), a loop type reactor (Peppel, *Industrial and Engineering*, 50, 767–770 (1958)) and a bubble column reactor(JP-A-6-345699 (U.S. Pat. No. 5,508,442)) have been proposed.

Another method for the production of monoethylene glycol has also been proposed in which ethylene carbonate is used as the intermediate and the reaction is carried out by allowing water to coexist in advance in the reaction system [JP-A-54-19905 (U.S. Pat. No. 4,160,116), JP-A-49-86308 (U.S. Pat. No. 3,922,314), JP-B-49-24448 (the term "JP-B" as used herein means an "examined Japanese patent publication"), JP-A-55-145623]. In this method, a mixture of ethylene carbonate and monoethylene glycol is first obtained by allowing ethylene oxide to react with carbon dioxide in water and then the remaining ethylene carbonate is completely hydrolyzed, so that monoethylene glycol as the product of interest can be obtained with a high yield without supplying excess amount of water. When water is present in this manner, the ethylene carbonation can be carried out markedly quickly and thus industrially advantageously, and water-containing ethylene oxide can be used as the material as it is.

Since hydrolysis of ethylene carbonate as the subsequent step is also carried out simultaneously in this method, load of the hydrolysis step can be reduced and the process therefore can be minimized.

In addition, the process can be simplified by directly combining it with an ethylene oxide production process. In general, production of ethylene oxide is carried out by the following method. Firstly, ethylene is converted into ethylene oxide by subjecting it to gas phase catalytic oxidation with oxygen in the presence of a silver catalyst, the thus obtained ethylene oxide-containing gas is allowed to contact with a large volume of water to effect absorption of ethylene oxide contained in the reaction gas by water and then ethylene oxide is recovered in the form of aqueous solution. Next, the thus obtained dilute aqueous solution of ethylene oxide (the ethylene oxide concentration is generally from 1 to 5% by weight) is heated under a reduced pressure to effect stripping and separation of ethylene oxide from the aqueous solution and then ethylene oxide is recovered from the top part of the reaction column. The absorbing water after the removal of ethylene oxide is cooled and again recycled to the absorption treatment. Thereafter, the aqueous mixture containing ethylene oxide as the main component thus obtained by the stripping treatment is subjected to distillation to remove water and thereby isolating and purifying ethylene oxide.

An important point of this method is to carry out the ethylene carbonate formation sufficiently faster than the side reaction which forms diethylene glycol from ethylene oxide and monoethylene glycol. For this purpose, it is essential to supply carbon dioxide to the liquid phase quickly and sufficiently in carrying out this reaction. However, nothing is known about a reactor in which the supply of carbon dioxide can be carried out sufficiently quickly and industrially safely and efficiently.

In addition, this reaction for producing ethylene carbonate from ethylene oxide generates considerably large heat of reaction so that it easily causes run away reaction. As a matter of course, the run away reaction is a problem to be avoided by all means, because it causes decomposition of catalyst and increases formation of aldehyde and the similar by-products, thereby exerting sheer adverse influences upon the quality of the ethylene glycol product.

In the case of the multiple pipe type reactors which are frequently used for this purpose, the reaction is not stable because of the difficulty in supplying each reaction pipe with carbon dioxide uniformly and of the inability to sufficiently cool the gas phase inside the pipes due to separation of carbon dioxide and reaction solution therein, so that the reaction sometimes does not progress smoothly and sometimes progresses too rapidly to cause run away reaction. A vessel type reactor equipped with an agitator requires considerable agitation power which still cannot dissolve carbon dioxide sufficiently in some cases. In addition, this type of reactor is not desirable in treating the toxic and explosive ethylene oxide from the viewpoint of safety, because its bearing part has a rolling friction which possibly causes leakage of gas or combusting and explosive reactions of ethylene oxide due to the frictional heat.

An object of the present invention is to provide a method for carrying out the reaction for obtaining a mixture of ethylene carbonate and monoethylene glycol safely and efficiently, in the process of selectively producing monoethylene glycol by allowing ethylene oxide to react with carbon dioxide in the presence of a carbonation catalyst and water, thereby obtaining said mixture, and then hydrolyzing the remaining ethylene carbonate.

Taking such actual circumstances into consideration, the inventors of the present invention have conducted intensive studies and found as a result of the efforts that stable reactions can be carried out by the use of a bubble column reactor, without accumulation of the heat of reaction or run away reaction. The present invention has been accomplished on the basis of this finding.

SUMMARY OF THE INVENTION

The present invention relates to a method for the production of monoethylene glycol, which is a method for producing ethylene glycol that comprises a carbonation step in which ethylene oxide is allowed to react with carbon dioxide in the presence of a carbonation catalyst thereby effecting formation of a reaction solution containing ethylene carbonate, a hydrolysis step in which the reaction solution is converted into an ethylene glycol aqueous solution by hydrolyzing ethylene carbonate in the reaction solution and a distillation step in which purified ethylene glycol and a catalyst solution containing the carbonation catalyst are obtained from the ethylene glycol aqueous solution by distillation, wherein the reaction is carried out in the presence of a carbonation catalyst using a bubble column reactor by supplying ethylene oxide, carbon dioxide and water into the reactor.

Figure 1:
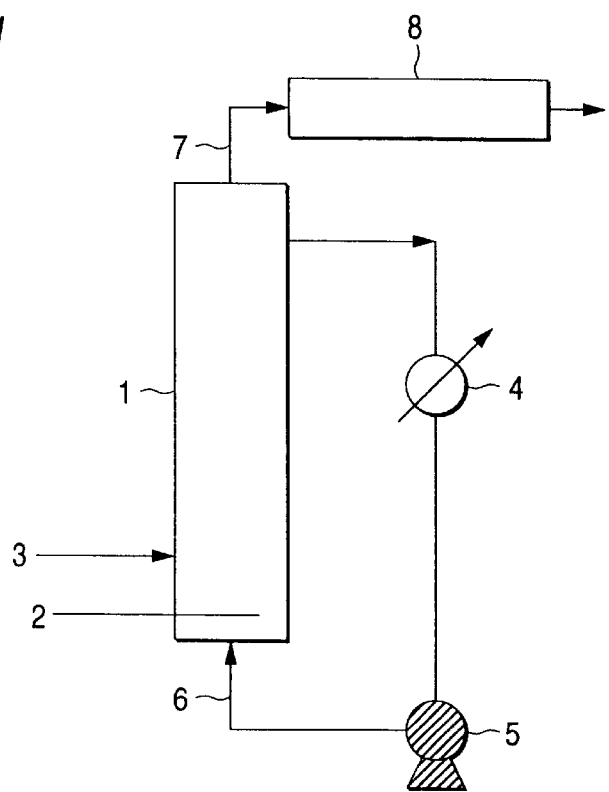
FIG. 1 is a flow sheet showing a mode of the method of the present invention.

The codes in the drawings respectively represent bubble column reactor (1), heat exchanger (4), circulating pump (5), first bubble column (9), second bubble column (10), plug flow reactor (11), first hydrolysis vessel (12), second hydrolysis vessel (13), dehydration distillation tower (14), evaporator (15), rectifying column (16), gas-liquid separator (17), heat exchanger (18), gas-liquid separator (19), heat exchanger (20), gas-liquid separator (21), condenser (22), compressor (23), carbon dioxide supplying pipe (24), supplying pipe of ethylene oxide and water (25), steam supplying pipe (26), steam supplying pipe (27) and catalyst solution circulating pipe (28).

DETAILED DESCRIPTION OF THE INVENTION

The following enumerates characteristics of the present invention.

It was revealed that industrially stable reaction of ethylene oxide can be carried out by the following combination of:

firstly using a bubble column reactor having a sparger on the reactor bottom, which renders possible quick and sufficient supply of carbon dioxide and avoidance of local heat reserve effected by the bubbles which vigorously agitate inside the reactor; and secondly allowing water to be present in the system, thereby rendering possible acceleration of carbonation reaction and smooth progress of hydrolyzing reaction which is endothermic reaction to absorb heat.

In addition, the presence of water enlarges heat capacity of the reaction solution, which is advantageous in preventing increment of temperature. Large latent heat of vaporization is also advantageous.

The bubble column reactor of the present invention is a reactor in which the reaction solution forms a continuous phase and the gas (carbon dioxide in the case of this invention) forms a dispersion phase, namely a reactor in which the substrate in the gas as the dispersion phase is dispersed in the continuous liquid phase, by introducing the gas into the reactor using a sparger arranged at the reactor bottom, and the reaction is carried out in the liquid phase. The liquid may be supplied from the upper side of the reactor to effect counter current contact or from the bottom side together with the gas to effect parallel current contact. With regard to the method for supplying the liquid and gas from the reactor bottom in the case of parallel contact, the liquid and gas may be introduced from separate piping systems or spargers or introduced into the reactor after mixing them in the sparger or in a piping arranged therein.

As the carbon dioxide sparger, a type which can generate a large number of small bubbles at a flow rate as small as possible is advantageous and desirable from the process point of view, because the circulating amount can be reduced while sufficiently keeping dissolution of carbon dioxide in the liquid phase. This effect may be obtained by a porous plate or a perforated pipe, but a gas-liquid simultaneous injection method is desirable in which the gas and liquid are mixed in the sparger or in a preceding reactor and supplied into the reaction system through the same injection nozzle.

Regarding the removal of heat of reaction, it can be effected by a method which uses a jacket, a method which uses an internal coil or a method in which a part of the reaction solution is taken out, cooled by introducing it into a heat exchanger and then recycled into the reactor.

As the carbonation catalyst, any known compound can be used optionally. Its examples include an alkali metal bromide or iodide (JP-B-38-23175), an alkaline earth metal halide (U.S. Pat. No. 2,667,497), an alkyl amine or quaternary ammonium (U.S. Pat. No. 2,773,070), an organic tin or a germanium or tellurium compound (JP-A-57-183784), a quaternary phosphonium (JP-A-58-126884 (U.S. Pat. No. 4,786,741)) and the like. A quaternary ammonium halide or a quaternary phosphonium halide is preferably used. Particularly, it is desirable to use a tetraalkylphosphonium halide in which the constituting alkyl group is an alkyl group having 1 to 4 carbon atoms, such as tetrabutylphosphonium iodide or the like. These compounds are supplied into the bottom part of the bubble column at a molar ratio of generally from 1/1,000 to 1/20 based on ethylene oxide.

It is desirable also to use such a quaternary ammonium halide or a quaternary phosphonium halide jointly with an alkali metal salt. As the alkali metal salt, it is desirable to use a carbonic acid salt, particularly potassium carbonate which has large solubility in ethylene glycol. In this connection, it is considered that, when an alkali metal halide or the like other alkali metal salt is used, the alkali metal exists in the form of alkali metal carbonate due to the presence of high pressure carbon dioxide in the reaction system. When an alkali metal salt is jointly used, formation of high boiling point substances is inhibited, and the hydrolyzing rate in the subsequent hydrolysis step is increased. It is desirable to use the alkali metal salt at a molar ratio of from 0.01 to 1 based on the quaternary ammonium salt or quaternary phosphonium salt which is the main catalyst.

Water is supplied in an amount of from 0.1 to 10 moles, preferably from 0.5 to 5 moles, more preferably from 0.8 to 1.2 moles, based on ethylene oxide. Smaller amount of water entails poor selectivity of monoethylene glycol. Also, if it is too large, the advantage from the conventional direct hydration method is lost.

Carbon dioxide is supplied in an amount of from 0.1 to 5 moles, preferably from 0.5 to 3 moles, more preferably from 0.8 to 2 moles, based on the material ethylene oxide. The supplying amount of carbon dioxide cannot be reduced too much, because not only it is a material for the formation of ethylene carbonate but also it is used to agitate the liquid in the reactor for the purpose of avoiding local accumulation of heat. On the other hand, its supply in excess amount increases required motive power of the carbon dioxide compressor, which is not advantageous from the process point of view. The catalyst concentration varies depending on the catalyst used, and in the case of a phosphonium halide salt such as tributylmethylphosphonium iodide, it can be used within the range of from 1/1,000 to 1/20 moles based on ethylene oxide.

The method of the present invention can be carried out at a reaction temperature of 70 to 200° C., but preferably from 100 to 150° C. in order to carry out the reaction smoothly and to reduce side reactions.

The reaction can be carried out under a pressure of from 5 to 50 kg/cm$^2$·G. Higher pressure is desirable because solubility of carbon dioxide increases, but required motive power of the compressor also increases. Preferred reaction pressure is within the range of from 10 to 30 kg/cm$^2$·G.

Retention time in the reactor is within the range of from 5 to 120 minutes. However, too short retention time is not desirable, because the concentration of remaining ethylene oxide becomes too large.

When the reaction of the present invention is carried out under continuous flow condition, ethylene oxide, water and a carbonation catalyst as materials are continuously supplied into the bubble column reactor, carbon dioxide is supplied from the bottom of the reactor through a sparger or the like means, and the reaction is carried out under predetermined conditions of temperature and time. In that case, in order to remove the heat of reaction, it is desirable to take out a part of the reaction solution from a side of the column head and cool it by a heat exchanger and then recycle it into the reactor. Also preferred is a mode in which the raw material gas is supplied into the reactor by mixing it with the circulating flow.

According to the present invention, it is desirable to carry out the carbonation step using a reactor comprising a reactor in which at least a first bubble column, a second bubble column and a plug flow reactor are connected in series. Since both of the formation reaction of ethylene carbonate from ethylene oxide and carbon dioxide and the formation reaction of ethylene carbonate and ethylene glycol from ethylene oxide, carbon dioxide and water are accompanied by the release of a large amount of heat of reaction, it is desirable as described in the foregoing to use a bubble column as the reactor in which the reaction solution is vigorously agitated so that local accumulation of heat in the reactor can be minimized. However, since inside of the bubble column is vigorously agitated, it is difficult to increase conversion of ethylene oxide. In order to increase conversion of ethylene oxide, it is necessary to increase the reaction temperature or prolong the reaction time. However, as described in the foregoing, each of these methods has a possibility of reducing the quality of finally obtained ethylene glycol. In a preferred mode of the present invention, at least a first bubble column and a second bubble column are connected in series, reaction materials and a catalyst are fed into the first bubble column, and a gas-liquid multi-phase (mixed-phase) flow comprising a liquid phase containing formed ethylene carbonate and a gas phase containing unreacted carbon dioxide is taken out from the top of the first bubble column and fed into the second bubble column from its bottom. When a third bubble column is further connected to the second bubble column, the gas-liquid multi-phase flow comprising gas phase and liquid phase is taken out from the top of the second bubble column and fed into the third bubble column from its bottom. A fourth bubble column can be used in the same manner, but the number of bubble columns is generally two or three, preferably two, in order to reduce facility cost. By using a plurality of bubble columns in this manner, a higher conversion can be obtained within shorter reaction time in comparison with the case of single bubble column.

According to the present invention, it is desirable to set reaction temperature in the first bubble column to a level of at least 10° C. lower than the reaction temperature in the second and additional bubble columns. Since all portion of ethylene oxide is fed into the first bubble column according to the present invention, concentration of ethylene oxide in the first bubble column is considerably higher than those in the second and additional bubble columns. In consequence, the reaction of ethylene oxide can be carried out at a high reaction rate even at a low reaction temperature. Reduction of reaction temperature in the first bubble column has advantages in that side reactions are reduced and the quality of finally obtained ethylene glycol is improved. It is desirable to set reaction temperature in the first bubble column to a level of 20° C. or more, particularly 30° C. or more, lower than the reaction temperature in the second and additional bubble columns. Even at such a temperature, the reaction in the first bubble column can be effected at a sufficiently high rate. In the first bubble column, it is desirable to carry out the reaction under such conditions that conversion of ethylene oxide at its outlet becomes a level of from 50 to 99.5%, particularly from 80 to 98%.

According to the present invention, all portion of ethylene oxide to be supplied to the reactor is fed into the first bubble column as described in the foregoing, and carbon dioxide and a catalyst are also fed into the first bubble column in all portions in general. If desired, portions of these materials can be fed into the second and additional bubble columns, but no particular benefits can be obtained thereby generally. Next, water is fed into the reactor to effect formation of ethylene glycol together with ethylene carbonate. Water is also fed into the first bubble column in one portion in general. According to the present invention, since the first bubble column is operated at a temperature lower than that of the second and additional bubble columns as described in the foregoing, generation of side reactions in the first bubble column is markedly reduced even when all portion of water is fed into the first bubble column. Ethylene oxide, carbon dioxide and water are fed into the bottom of the bubble column. These may be fed each independently or together with other materials.

According to the present invention, it is desirable that at least 99%, particularly 99.5% or more, of the supplied ethylene oxide is allowed to undergo the reaction in the bubble columns. The multi-phase flow of liquid phase and gas phase discharged from the top of the final (downstremmost) bubble column is separated into gas phase and liquid phase by applying it to a gas-liquid separator. The gas phase mainly comprises unreacted carbon dioxide and is generally cooled and fed into the bottom of the first bubble column by compressing it with a compressor. In order to prevent accumulation of volatile impurities, it is desirable to allow a part of the gas phase to be purged from the system. The liquid phase discharged from the gas-liquid separator is fed into the succeeding plug flow reactor where the dissolved ethylene oxide is converted into ethylene carbonate and/or ethylene glycol. In this connection, when the liquid phase and the gas phase can be taken out separately from the final bubble column, the liquid phase thus taken out can be fed directly into the plug flow reactor.

According to the present invention, the greater part of ethylene oxide is allowed to undergo the reaction in bubble columns as described in the foregoing, but, due to the characteristics of the bubble columns, a small amount of ethylene oxide is dissolved in the liquid phase obtained from the final bubble column. When this liquid phase is directly subjected to hydrolysis, it causes a loss of ethylene oxide. In the plug flow reactor, it is desirable to set reaction time and other reaction conditions to such levels that concentration of ethylene oxide in the reaction solution becomes 100 ppm or less, particularly 20 ppm or less. With regard to reaction conditions in plug flow reactor, the reaction temperature is generally from 70 to 200° C., preferably from 100 to 170° C., and the reaction pressure is generally from 5 to 50 $kg/cm^2G$, preferably from 10 to 30 $kg/cm^2G$. In this connection, the cooling treatment is not generally necessary for the plug flow reactor because of small heat generation.

The reaction solution discharged from the plug flow reactor is fed into a hydrolysis apparatus where ethylene carbonate in the reaction solution is hydrolyzed into ethylene glycol. This hydrolysis reaction can be carried out in the usual way. An apparatus in which a plurality of sections, such as a plurality of hydrolysis vessels connected in series, are arranged in a series is used as a preferred hydrolysis apparatus, so that the reaction solution in the hydrolysis apparatus flows closely to the plug flow. In addition, in order to accelerate the hydrolysis reaction, it is desirable to increase the temperature or reduce the pressure as the reaction solution approaches the outlet by its flow. The hydrolysis temperature is generally from 80 to 200° C., preferably from 100 to 180° C. The hydrolysis temperature if too high would reduce the quality of finally obtained ethylene glycol. The pressure may be optionally set within such a range that the reaction solution does not boil. It is desirable to carry out the hydrolysis reaction until ethylene carbonate disappears virtually completely.

By distillation, purified ethylene glycol and a catalyst solution containing the carbonation catalyst are obtained from the ethylene glycol aqueous solution discharged from the hydrolysis apparatus. The former is the product, and the latter is recycled as the catalyst into the reactor. Preferably, this distillation is carried out via the distillation-catalyst separation-precision distillation steps described in Japanese Patent Application No. 10-364504. According to this method, an ethylene glycol aqueous solution is firstly distilled under a reduced pressure in a dehydration distillation tower to evaporate water, thereby obtaining a dehydrated hydrolysate solution. Next, the thus dehydrated hydrolysate solution is fed into an evaporator by which the greater part of ethylene glycol, diethylene glycol and the homologous high boiling point substances are evaporated under a reduced pressure, and the thus obtained evaporation residue comprised, mainly, the catalyst and ethylene glycol, and small amounts of high boiling point substances is circulated as a catalyst solution into the reactor. According to this method, high temperature vapor is obtained from the evaporator, so that heat recovery therefrom can be made easily. Also, since the greater part of high boiling point substances are evaporated by the evaporator, accumulation of the high boiling point substances in the reaction system can be avoided. In addition, composition and concentration of the catalyst solution obtained as the evaporation residue can be adjusted by controlling the quantity of heat to be supplied.

The vapor comprising ethylene glycol and high boiling point substances is condensed by a heat exchanger and distilled under a reduced pressure in a rectifying column, and purified ethylene glycol is obtained from the column head. Depending on the operation conditions of the rectifying column, distillation residue discharged from the column bottom is distilled in a recovery column to obtain ethylene glycol as the distillate which is recycled into the rectifying column. The distillation residue is used as fuel, but, if desired, diethylene glycol and the like can be recovered by its distillation.

EXAMPLES

The following inventive and comparative examples are provided to further illustrate the present invention, but the invention is not restricted by these examples unless overstepping its gist. In this connection, conversion ratio and selectivity of ethylene oxide are mol %.

EXAMPLE 1

(1) Ethylene Carbonation Reaction Step

Continuous reaction was carried out using a bubble column reactor (1 in FIG. 1) having an inner diameter of 20 cm and a tower height of 200 cm. Blowing of carbon dioxide was carried out from the line 2 through a perforated pipe type sparger. Amounts of the supplied materials were carbon dioxide: 140 kg/H, ethylene oxide: 62 kg/H and water: 50 kg/H ($CO_2$/EO=2.2 (mol/mol), $H_2O$/EO=2.0 (mol/mol)) . As the catalyst, 4.5 kg/H of tributylmethylphosphonium iodide was fed into the reactor. The catalyst and other materials than carbon dioxide were directly fed into the reactor from the line 3. A part of the reaction solution was taken out from a side of the tower top, fed into the heat exchanger 4 to remove heat of reaction and then recycled into the reactor 1 through the line 6 by the circulating pump 5. The materials were continuously supplied, and the formed solution was discharged from the system by the line 7 on the tower head, together with excessively supplied carbon dioxide.

The experiment was carried out at a temperature of 150° C. and under a pressure of 20 $kg/cm^2 \cdot G$. The EO concentration in the reaction solution obtained from the line 7 was 0.4% by weight, and the carbon dioxide concentration (calculated value) in the solution was 0.56% by weight. The selectivity for ethylene oxide calculated from the composition of the thus obtained reaction solution was monoethylene glycol: 70.2%, ethylene carbonate: 25.2%, DEG: 4.2% and TEG: 0.4%.

(2) Consumption of Unreacted Ethylene Oxide and Purification of Monoethylene Glycol A heat-insulated piping line 8 of 5 m in length and 5 cm in diameter was connected to the line 7, and the reaction solution obtained when reacted at 150° C. in the above step (1) was passed through the lines continuously. Temperature of the reaction solution discharged from the line 8 was 152° C. Ethylene oxide was not detected from the discharged reaction solution. Next, ethylene carbonate in the reaction solution obtained at a temperature of 150° C. and under a pressure of 3 kg/cm$^2$·G was completely hydrolyzed and then high quality monoethylene glycol was obtained by its isolation and purification by means of distillation.

EXAMPLE 2

Figure 2:
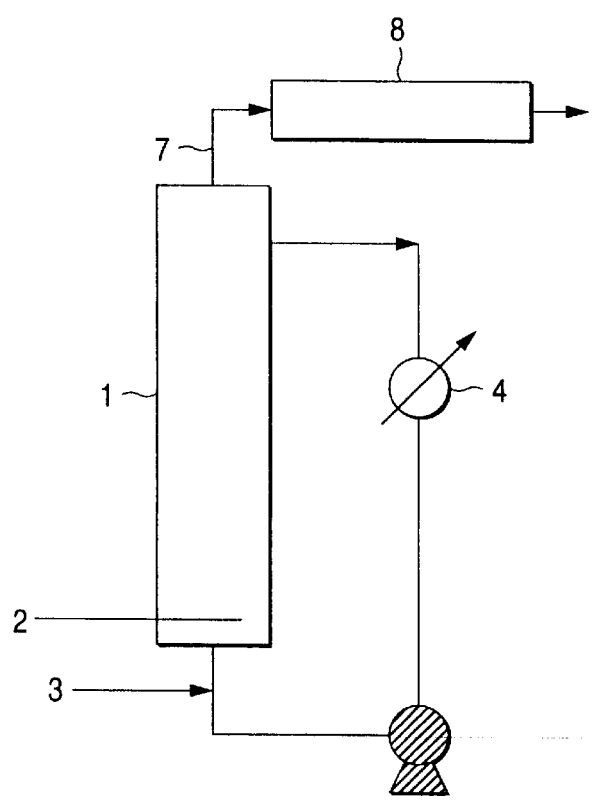
FIG. 2 is a flow sheet showing another mode of the method of the present invention.
Figure 3:
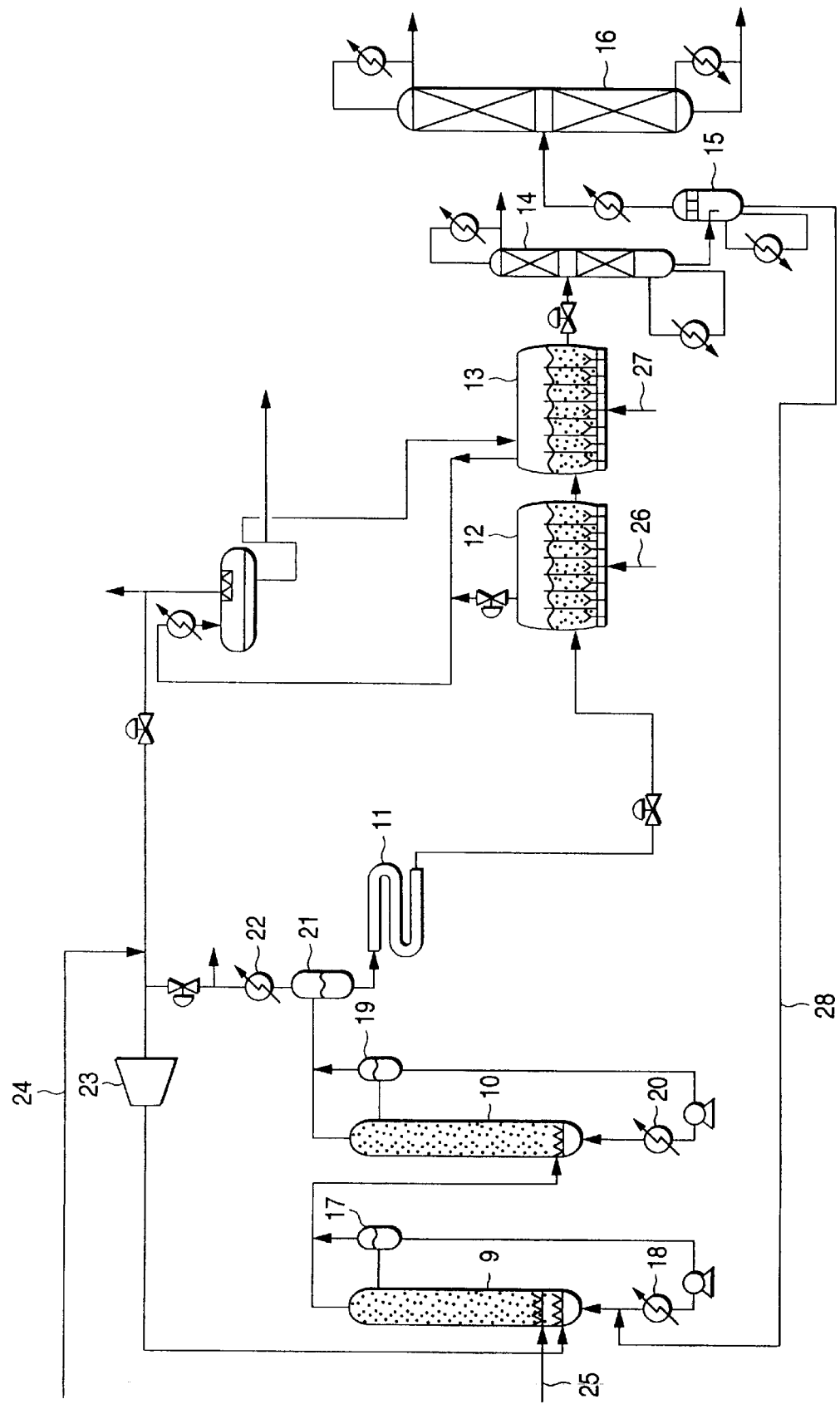
FIG. 3 is a flow sheet showing still another mode of the method of the present invention.

The same test of Example 1 was carried out using the same apparatus (cf. FIG. 2), except that blowing of carbon dioxide was carried out by gas-liquid simultaneous blowing. Amounts of supplied materials were the same as those of Example 1. As the catalyst, 4.5 kg/H of tributylmethylphosphonium iodide was fed into the reactor. The test conditions were also the same. Stable operation was possible, and the conversion ratio of ethylene oxide was 99% or more. The selectivity for ethylene oxide calculated from the composition of the thus obtained reaction solution was monoethylene glycol: 62.3%, ethylene carbonate: 35.3%, DEG: 2.3% and TEG: 0.1%. After treating unreacted ethylene oxide in the same manner as described in Example 1, ethylene carbonate in the reaction solution obtained at a temperature of 150° C. and under a pressure of 3 kg/cm$^2$·G was completely hydrolyzed and then fiber grade high quality monoethylene glycol was obtained by its isolation and purification by means of distillation in the same manner as described in Example 1.

EXAMPLE 3

Using a reaction apparatus constructed by serially connecting a first bubble column, a second bubble column and a gas-liquid separator, each having a diameter of 20 cm and an effective height of 200 cm, and a pipe type reactor of 6 cm in diameter and 200 cm, a reaction solution containing ethylene carbonate and ethylene glycol was formed from ethylene oxide, carbon dioxide and water. Each bubble column was equipped with an external circulating type cooler.

Into the bottom of the first bubble column were continuously fed ethylene oxide at a rate of 62 kg/Hr, carbon dioxide at 140 kg/Hr, water at 50 kg/Hr, tetrabutylphosphonium iodide as the catalyst at 2.8 kg/Hr and potassium carbonate at 0.11 kg/Hr. In this case, tetrabutylphosphonium iodide and potassium carbonate were dissolved in ethylene glycol and supplied as a solution containing about 47% by weight of the former and about 1.9% by weight of the latter. The gas-liquid multi-phase flow discharged from the top of the first bubble column was fed into the bottom of the second bubble column, and the gas-liquid multi-phase flow discharged from the head of the second bubble column was fed into the gas-liquid separator. The liquid phase from the gas-liquid separator was fed into the tublar reactor, and the gas phase was cooled and recycled into the bottom of the first bubble column via a compressor together with carbon dioxide to be supplied freshly. Temperature in the first bubble column was controlled at 110° C., and that of the second bubble column at 150° C. The tublar reactor was covered with a heat insulating material, and its temperature was not controlled but maintained at about 150° C. because of small generation of heat. Also, pressure in the gas-liquid separator was controlled at 20 kg/cm$^2$·G. Pressure in the bubble columns and the tublar reactor was not particularly controlled, but it can be considered that the pressure is 20 kg/cm$^2$·G throughout the reaction system because of no evident drop in pressure. The conversion of ethylene oxide was about 95% in the first bubble column and about 99.5% at the outlet of the second bubble column. Concentration of ethylene oxide in the reaction solution at the outlet of the pipe type reactor was about 70 ppm.

The reaction solution discharged from the tublar reactor was continuously fed into a hydrolysis apparatus and hydrolyzed. The hydrolysis apparatus was composed of a first vessel and a second vessel connected in series, and the first vessel was maintained at 3.5 kg/cm$^2$·G and 150° C., and the second vessel at 1.8 kg/cm$^2$·G and 150° C., by blowing steam into each vessel. Retention time in the hydrolysis vessel was about 1 hour, and the ethylene glycol aqueous solution discharged from the hydrolysis apparatus contained substantially no ethylene carbonate (10 ppm or less). Selectivity of ethylene glycol calculated from the composition of the ethylene glycol aqueous solution discharged from the hydrolysis apparatus reached about 99.1%. This aqueous solution was fed into a dehydration distillation tower and distilled under a tower head pressure of 82 mmHg at the column top and a temperature of 140° C. at the column bottom while distilling off water from the top. The dehydrated reaction solution discharged from the tower bottom was fed into an evaporator kept at 140° C. and 62 mmHg to effect evaporation of the greater part of ethylene glycol and high boiling point substances. The energy necessary for the evaporation was supplied by a reboiler attached to the evaporator. The ethylene glycol solution recovered as evaporation residue containing the catalyst and a small amount of high boiling point substances (concentration of tetrabutylphosphonium iodide, about 47% by weight) was recycled into the first bubble column as a catalyst solution. The vapor discharged from the evaporator was condensed and heat-recovered by a heat exchanger and fed into a rectifying tower where distillation was carried out under a column top pressure of 52 mmHg and at a column bottom temperature of 160° C. to discharge purified ethylene glycol as a distillate from the tower head. The thus obtained ethylene glycol showed a high purity and satisfied the fiber grade standard.

COMPARATIVE EXAMPLE 1

Example 1 was repeated using the same apparatus, except that water was not supplied. Ethylene carbonate was dissolved and charged in advance in the reactor. Amounts of materials supplied were carbon dioxide: 140 kg/H and ethylene oxide: 62 kg/H. Tributylmethylphosphonium iodide was fed as the catalyst into the reactor at a rate of 4.5 kg/H. The test was carried out at a temperature of 150° C. and under a pressure of 20 kg/cm$^2$·G. Though run away reaction was avoided, conversion of ethylene oxide was so slow that conversion ratio of ethylene oxide reached only 33%.

COMPARATIVE EXAMPLE 2

Continuous reaction was carried out using an autoclave of 25 cm in inner diameter and 50 cm in tower height, which is equipped with an electromagnetic guidance agitator and with a coiled tube for heat exchange inside. Carbon dioxide was blown into the gas phase. Amounts of the supplied materials were carbon dioxide: 37 kg/H, ethylene oxide: 37 kg/H and water: 30 kg/H (CO$_2$/EO=1 (mol/mol), H$_2$O/EO= 2.0 (mol/mol)). As the catalyst, 2.7 kg/H of tributylmethylphosphonium iodide was fed into the reactor. The catalyst and other materials than carbon dioxide were fed into the reactor from a separate line from the one for carbon dioxide.

The reaction mixture was stirred with the agitator at 400 rpm. The raw materials were continuously supplied, and the reaction mixture was discharged from the system together with excessively supplied carbon dioxide.

The experiment was carried out continuously for one week at a temperature of 150° C. and under a pressure of 20 kg/cm$^2$·G. Conversion of ethylene oxide reached merely 98%. The selectivity for ethylene oxide calculated from the composition of the thus obtained reaction solution was monoethylene glycol: 81.8%, ethylene carbonate: 10.2%, DEG: 7.2% and TEG: 0.8%. The reaction solution colored pale yellow and had an aldehyde odor.

What is claimed is:

1. A method for producing monoethylene glycol, which comprises:
   a carbonation step in which ethylene oxide is allowed to react with carbon dioxide in the presence of a carbonation catalyst, to form a reaction solution containing ethylene carbonate;
   a hydrolysis step in which the reaction solution is converted into an ethylene glycol aqueous solution by hydrolyzing ethylene carbonate in the reaction solution; and
   a distillation step in which purified ethylene glycol and a catalyst solution containing the carbonation catalyst are obtained from the ethylene glycol aqueous solution by distillation,
   wherein the reaction is carried out in the presence of a carbonation catalyst using a bubble column reactor by supplying ethylene oxide, carbon dioxide and water into the reactor.

2. The method according to claim 1, wherein the molar ratio of carbon dioxide to ethylene oxide to be supplied to the reactor is from 0.1 to 5, and the molar ratio of water to ethylene oxide is from 0.1 to 10.

3. The method according to claim 1, wherein the reaction temperature is from 70 to 200° C., and the reaction pressure is from 5 to 50 kg/cm$^2$·G.

4. The method according to claim 1, wherein a part of the reaction solution is taken out from the upper side of the reactor and cycled through a circulation line into the bottom of the reactor, and the raw material gas is fed into the reactor through the circulation line.

5. The method according to claim 2, wherein a part of the reaction solution is taken out from the upper side of the reactor and cycled through a circulation line into the bottom of the reactor, and the raw material gas is fed into the reactor through the circulation line.

6. The method according to claim 3, wherein a part of the reaction solution is taken out from the upper side of the reactor and cycled through a circulation line into the bottom of the reactor, and the raw material gas is fed into the reactor through the circulation line.

7. The method according to claim 1, wherein the carbonation step is carried out using a reactor which comprises serially connected bubble columns including at least two bubble columns and a plug flow reactor connected downstream from the bubble columns, under the following conditions:

(1) ethylene oxide and carbon dioxide are continuously fed into the bottom of the first bubble column, and the formed gas-liquid multi-phase flow comprising a liquid phase containing ethylene carbonate and a gas phase containing unreacted carbon dioxide is taken out from the column top and fed into the bottom of the second bubble column;

(2) in the second and any suceeding bubble columns, the temperature is maintained to be at least 10° C. higher than that the first tubble column, and the formed liquid phase containing ethylene carbonate and gas phase containing unreacted carbon dioxide are taken out as a gas-liquid multi-phase flow from each column top and fed into the bottom of the next bubble column excluding the downstream-most bubble column; and (3) the liquid phase separated from the gas phase is taken out from the downstream-most bubble column and fed into the plug flow reactor, or the liquid phase and gas phase are taken out from the tower head as a multi-phase flow and subjected to gas-liquid separation using a gas-liquid separator and then the thus obtained liquid phase is fed into the plug flow reactor.

8. The method according to claim 7, wherein ethylene oxide, carbon dioxide and water are continuously fed into the bottom of the first bubble column in such amounts that the molar ratio of carbon dioxide to ethylene oxide is from 0.1 to 5 and the molar ratio of water to ethylene oxide is from 0.1 to 10.

9. The method according to claim 7, wherein the reaction is carried out under such a condition that the reaction ratio of ethylene oxide at the outlet of the first bubble column is from 50 to 99.5%.

10. The method according to claim 8, wherein the reaction is carried out under such a condition that the conversion of ethylene oxide at the outlet of the first bubble column is from 50 to 99.5%.

* * * * *